(12) United States Patent
Tung et al.

(10) Patent No.: US 7,438,852 B2
(45) Date of Patent: Oct. 21, 2008

(54) SAMPLE COLLECTION CUP WITH INTEGRATED SAMPLE ANALYSIS SYSTEM

(75) Inventors: Hsiaoho Edward Tung, San Diego, CA (US); Yuchang Wu, Hangzhou (CN); Jeling Dai, Hanzhou (CN); Ying Yang, Hanzhou (CN)

(73) Assignee: Inverness Medical Switzerland GmbH, Zug (CH)

( * ) Notice: Subject to any disclaimer, the term of this patent is extended or adjusted under 35 U.S.C. 154(b) by 463 days.

(21) Appl. No.: 10/989,935

(22) Filed: Nov. 15, 2004

(65) Prior Publication Data

US 2005/0106750 A1    May 19, 2005

Related U.S. Application Data

(60) Provisional application No. 60/520,237, filed on Nov. 14, 2003.

(51) Int. Cl.
*G01N 33/00* (2006.01)
(52) U.S. Cl. .............................. 422/61; 422/55; 422/56; 422/58; 422/100; 422/102
(58) Field of Classification Search ............. 422/50–58, 422/68.1, 99–103
See application file for complete search history.

(56) References Cited

U.S. PATENT DOCUMENTS

| | | | |
|---|---|---|---|
| 4,409,989 A | 10/1983 | Larribas | |
| 5,119,830 A * | 6/1992 | Davis | 600/584 |
| 5,238,652 A | 8/1993 | Sun | |
| 5,464,775 A | 11/1995 | Smith | |
| 5,591,401 A * | 1/1997 | Sayles | 422/58 |
| 5,595,187 A * | 1/1997 | Davis | 600/584 |
| 5,606,116 A | 2/1997 | Yoneda | |
| 5,874,216 A | 2/1999 | Mapes | |
| 5,942,442 A | 8/1999 | Di Cesare | |
| D423,110 S | 4/2000 | Cipkowski | |
| 6,074,606 A * | 6/2000 | Sayles | 422/58 |
| D430,303 S | 8/2000 | Cipkowski | |
| 6,168,758 B1 * | 1/2001 | Forsberg et al. | 422/61 |
| 6,291,178 B1 | 9/2001 | Schnider | |
| 6,342,183 B1 * | 1/2002 | Lappe et al. | 422/58 |
| 6,372,515 B1 | 4/2002 | Casterlin | |

(Continued)

FOREIGN PATENT DOCUMENTS

EP        0709675 B1      3/2002

(Continued)

*Primary Examiner*—Sam P Siefke
(74) *Attorney, Agent, or Firm*—Fred C. Hernandez; Mintz Levin Cohn Ferris Glovsky and Popeo PC (57) ABSTRACT

The present invention is directed to devices and methods for collecting liquid samples and of testing the sample for the presence of an analyte of interest and/or a physical property. In one embodiment the device is a urine cup having an interior for containing a liquid sample, a lid, and a chamber for holding liquid. The device contains a test component for determining the presence of an analyte in the liquid sample and/or a physical property. A tube is immersed in liquid sample when the device is filled with liquid sample to be tested. When the lid is applied to the device (e.g., by screwing or snapping on), liquid sample is forced through the tube and into the chamber holding the test component.

28 Claims, 8 Drawing Sheets

U.S. PATENT DOCUMENTS

| | | |
|---|---|---|
| 6,376,195 B1 | 4/2002 | Mapes |
| 6,383,736 B1 | 5/2002 | Titmas |
| 6,406,922 B2 | 6/2002 | Casterlin |
| 6,514,769 B2 | 2/2003 | Lee |
| 6,528,323 B1 | 3/2003 | Thayer |
| 6,548,019 B1 | 4/2003 | Lee |
| 6,663,831 B2 | 12/2003 | Konecke |
| 6,680,027 B2 * | 1/2004 | Kang et al. .................. 422/58 |
| 6,730,268 B2 | 5/2004 | Lee |
| 2002/0001854 A1 | 1/2002 | Lee |
| 2002/0046614 A1 | 4/2002 | Alley |
| 2002/0146346 A1 | 10/2002 | Konecke |
| 2003/0007892 A1 | 1/2003 | Smith |
| 2003/0129088 A1 | 7/2003 | Lee |
| 2004/0132091 A1 | 7/2004 | Ramsey |
| 2004/0133128 A1 | 7/2004 | Guan |
| 2004/0184965 A1 | 9/2004 | Smith |
| 2005/0008538 A1 | 1/2005 | Anderson |
| 2005/0009203 A1 | 1/2005 | Wong |
| 2005/0053519 A1 | 3/2005 | Smith |
| 2005/0106750 A1 | 5/2005 | Tung |
| 2005/0112024 A1 | 5/2005 | Guo |

FOREIGN PATENT DOCUMENTS

| | | |
|---|---|---|
| EP | 1028806 B1 | 7/2003 |
| WO | WO9119980 A1 | 12/1991 |
| WO | WO9731269 A1 | 8/1997 |
| WO | WO0029111 A1 | 5/2000 |
| WO | WO0062060 A2 | 10/2000 |
| WO | WO0063697 A1 | 10/2000 |
| WO | WO0165230 A2 | 9/2001 |
| WO | WO0189697 A2 | 11/2001 |
| WO | WO0189697 A3 | 11/2001 |
| WO | WO0224337 A1 | 3/2002 |
| WO | WO02082040 A2 | 10/2002 |
| WO | WO2005006959 A2 | 1/2005 |
| WO | WO2005050168 A2 | 6/2005 |
| WO | WO2005050169 A2 | 6/2005 |

* cited by examiner

SAMPLE COLLECTION CUP WITH INTEGRATED SAMPLE ANALYSIS SYSTEM

This application claims priority to U.S. provisional patent application Ser. No. 60/520,237, filed Nov. 14, 2003, which is hereby incorporated by reference in its entirety, including all Tables, Figures, and Claims.

FIELD OF THE INVENTION

The present invention is directed to containers for the collection and analysis of fluids for the presence of analytes or adulterants, and other physical properties.

BACKGROUND OF THE INVENTION

The following Background of the Invention is intended to aid the reader in understanding the invention and is not admitted to be prior art.

Illicit drug use is an established and growing problem in our society. In 2003, the US Department of Health and Human Services found that an estimated 19.5 million Americans or 8.2 percent of the population aged 12 or older, were current illicit drug users. Current illicit drug use means use of an illicit drug during the month prior to the US Department of Health and Human Services survey interview. Marijuana was found to be the most commonly used illicit drug, with a rate of 6.2 percent (14.6 million). An estimated 2.3 million persons (1.0 percent) were current cocaine users, 604,000 of whom used crack. Hallucinogens were used by 1.0 million persons, and there were an estimated 119,000 current heroin users.

To combat and monitor this problem, drug testing has become standard procedure in a variety of settings, such as employment, school, sports, law enforcement, and the like. To facilitate this effort, a drug-testing industry has emerged. This industry provides a variety of drug testing products. A typical product is a urine collection cup incorporating analysis tests. These devices can be complicated and difficult or messy to use, or they may pose special problems of sample adulteration by the subject trying to hide their recent drug abuse.

There is therefore a need for better methods and apparatuses for performing sample collection and testing.

SUMMARY OF THE INVENTION

The present invention is directed to devices and methods for collecting liquid samples and of testing the sample for the presence of an analyte of interest and/or a physical property. In one embodiment the device is a urine cup having an interior for containing a liquid sample, a lid, and a chamber for holding fluid. The device contains a test component for determining the presence of an analyte in the fluid sample and/or a physical property. A tube is immersed in liquid sample when the device is filled with liquid sample to be tested. When the lid is applied to the device (e.g., by screwing on or snapping on), sample is forced through the tube and into the chamber holding the test component.

Thus, in a first aspect the present invention provides a liquid sample collection and analysis device that contains a cup having an interior for containing a liquid sample, a lid which fits onto the cup, and a chamber containing one or more test components, which contain reagents for detecting an analyte of interest in the sample. In one embodiment the test component has a sample application zone and a detection zone. The device also has a tube that provides a passage between the interior of the cup and the chamber, which transports a portion of the sample from the interior of the cup into the chamber. In one embodiment the chamber is contained within the lid and contains a channel having an inlet for receiving liquid sample from the tube. The channel can also have an outlet for delivering liquid sample from the inlet to the test component. The chamber can also have wicking paper in fluid communication with the outlet and the sample application zone of the test component. In one embodiment the lid and the cup have screw threads and, when the screw threads are fully engaged, an airtight seal is formed between the cup and lid. The cup and lid can also have stop tabs that abut one another when the screw threads are fully engaged. "Screw threads" refers to indentations and/or protrusions on the rim of the cup and lid. The screw threads on the rim and lid are complementary and mated with each other so that the lid is not removable from the cup without torsional motion of the lid or cup, and the screw threads are thereby engaged. The screw threads bring the lid and cup together when the lid is torsionally rotated, forming an airtight seal when the screw threads are fully engaged. In embodiments where screw threads are used, the screw threads are "fully engaged" when the lid is rotated onto the lip of the cup and the stop tabs on the lid and cup meet. In other embodiments no screw threads are used, and protrusions and/or indentations can be present on the rim of the cup. In these embodiments the lid can be snapped onto position on the top of the cup or otherwise secured to the cup.

In another embodiment the device has a depressible button, which has a depressed position and a raised position such that, when the screw threads are fully engaged, air pressure in the cup is higher when the button is in the depressed position relative to the air pressure when the button is in the raised position. The test component can be a test strip containing specific binding molecules immobilized on the test strip. The device can also have a sealable opening in the lid for extracting liquid sample when the lid is mated to the cup. In one embodiment the test components are test strips and the lid has a plurality of test strips for determining the presence or absence of a plurality of analytes of interest in the sample. The test strips can be suitable for any assay form, such as an immunoassay, a chemical test, a test for a physical property of the liquid sample, and other tests of interest. When the test is for a physical property, the test can be for any physical property of the sample such as, for example, temperature, specific gravity, pH, oxidant contamination, glutaraldehyde contamination, nitrite contamination, ascorbic acid contamination, and creatinine concentration. In one embodiment the lid is principally flat on one side.

The "chamber" refers to an enclosed space or compartment that contains the test component. In one embodiment the chamber is contained within the lid. In other embodiments the chamber can be separate from the lid, but functions in an equivalent manner to a chamber contained within the lid. For example, in various embodiments the chamber can be contained in the interior of the cup, or outside the cup in a second compartment. The term "transparent" indicates a material that allows the passage of light so that objects behind the transparent material can be seen with the unaided eye in ordinary room lighting, and a user can see and read the test results below the transparent window. In "fluid communication" means that liquid can flow from one structure to another, when two structures are in fluid communication. Thus, in one embodiment of the present invention the outlet from the passageway and the sample application zone are in fluid communication, because liquid flows from the outlet of the passageway and is imbibed or absorbed by the sample application zone. The term "cup" includes not only the conventional configuration of a substantially circular or oval container, but also includes containers of any shape. Thus, the cup can have a square configuration, or any configuration consistent with performance of its function. Also, the lid of the device can have screw threads as described herein, but can also be snapped onto the cup portion of the device, or even applied in the fashion of a cork where the lid is squeezed into the interior space of the cup and held in place by the expansive forces of the lid material. When screw threads are present they need not be of any specific depth and a portion of a turn of the lid on the cup can fully engage the screw threads, or several turns. But in some embodiments the cup will be circular, as will the lid.

In one embodiment, the chamber has a network of channels having an inlet connected to the tube and outlets. A "channel" is a long narrow groove or furrow. In the context of this application a "channel" directs the fluid sample from one location to another, in a manner similar to that of irrigation channels that are cut to direct the flow of water in a field. More than one channel may be used to form a "network," which directs the fluid to multiple terminal locations, as opposed to a single termination point of a single channel. In general, channel networks are branching structures, from a larger channel to smaller sub-channels. Fluid enters the channel network at the "inlet." The terminus of a channel or sub-channel, where the fluid flows out, is referred to as an "outlet."

In certain embodiments, the test strips are lateral flow test strips. "Lateral flow" means that fluid sample is absorbed or imbibed by one end of the test strip. As the sample is absorbed, it travels towards the opposite end of the test strip by capillary action. In one embodiment of the present invention, each test strip has a sample application zone in fluid communication with the outlet of the channel network. The sample is absorbed by the sample application zone. As the sample moves through the test strip, the sample reacts with reagents in or on the test strip, and then the sample passes through a results zone, where the test results may be read. In additional embodiments, an absorbent wicking paper may be provided adjacent to and in fluid communication with the outlets and the test strips.

If fluid can pass between two structures, either directly or indirectly, the two structures are said to be in "fluid communication" with each other. For example, an outlet of the channel network and the sample application zone of a test strip are in direct fluid communication if they are adjacent to each other, with no intervening structure, and the fluid passes directly from the outlet to the sample application zone. Often, but not always, the two structures are touching each other. On the other hand, the outlet and sample application zone are in indirect fluid communication if a wicking paper is placed between the outlet and the sample application zone. In this situation, there is still fluid communication, but the fluid passes from the outlet, to the wicking paper, and finally to the sample application zone.

In another embodiment, the cup rim and the lid have complementary annular threads, which mate when the lid is screwed onto the cup, an O-ring and optionally engageable stop tabs. When the threads of the cup and the lid are mated and the lid is screwed all the way onto the cup, an airtight seal is created between the lid and the cup. When the seal is "airtight" no air or gas can pass either in our out of the closed cup at atmospheric pressure. When the screw threads are fully engaged, air pressure in the cup is higher relative to the air pressure when the screw threads are not fully engaged. When the stop tabs are mated, an air tight seal is created between the cup and the lid. Mating of the stop tabs is a visual indicator that the screw threads are fully engaged. When the threads are fully engaged, an airtight seal is formed between the cup and the lid. Similarly, when the stop tabs are mated an airtight seal is formed between the cup and the lid.

In further embodiments, the cup has a depressible button having a depressed position and a raised position. When the screw threads are fully engaged, air pressure in the cup is higher when the button is in the depressed position relative to the air pressure when the button is in the raised position.

In another embodiment, the lid has a sealable opening. The sealable opening provides access to the sample so that sample can be removed from the interior of the cup without removing the lid.

In yet another embodiment, the test strips each have a sample application zone and a results zone. The test strip may detect analytes in the sample or measure a physical property of the sample. Analyte detection test strips have specific reagents for detecting the presence or absence of an analyte in the sample. The test strip may be an immunoassay and have specific binding molecules immobilized on the test strip. Alternatively, the test strip may be a chemical test. Physical property test strips can test temperature, specific gravity, pH, oxidant contamination, glutaraldehyde contamination, nitrite contamination, ascorbic acid contamination, creatinine concentration, and any other physical property for which a test component exists or can be made. Physical property test strips also have specific reagents for detecting these properties of the sample. Often, but not necessarily, these are chemical test strips.

In another aspect the present invention provides a liquid sample collection and analysis device, which has a cup having an interior for containing a liquid sample, and a rim having first screw threads and a first stop tab. The device also has a lid having a chamber, a test strip having a sample application zone and a detection zone, a transparent window and a side curtain having second screw threads and a second stop tab. There is also a tube in fluid communication with the interior of the cup and the chamber, which transports a portion of the sample from the cup interior into the chamber. The first screw threads and second screw threads are complementary, and fully engageable. All of the embodiments and features discussed herein are also applicable to this device, as well as other devices described herein. In one embodiment, the chamber contains a wicking paper in fluid communication with the outlet and the sample application zone of the test strip.

In a further embodiment, the cup has a button that can be manually depressed by the operator. The button has a raised position and a depressed position. When the cup is sealed, as described herein, and the button is in the depressed position, the sealed cup has a higher internal air pressure relative to a sealed cup with the button in the raised position. The lid may also contain a sealable opening. The opening has a push plug or screw plug and provides access to sample in the interior of the cup without the need to unscrew or otherwise remove the lid.

In yet another embodiment, the test strip has specific binding molecules immobilized thereon. The test strip may be a chemical test or an immunoassay. The test results can be visually determined. The test strip may determine a physical property of the liquid sample, such as but not limited to, temperature, specific gravity, pH, oxidant contamination, glutaraldehyde contamination, nitrite contamination, ascorbic acid contamination or creatinine concentration.

In another aspect the present invention provides methods of detecting the presence of an analyte in a fluid sample. The methods involve introducing a liquid sample into a cup having an interior for containing the liquid sample, a lid for containing liquid sample in the cup and having a first set of screw threads, a rim comprising a second set of screw threads, a chamber having at least one test component, which components contain a sample application zone, a detection zone, and reagents for detecting an analyte of interest; and a passage for transferring liquid sample between the interior of the cup and the chamber. The liquid sample is allowed to flow through the passage from the interior of the cup to the chamber and to contact a test component. The presence or absence of analyte in the liquid sample is therefore determined. In some embodiments the methods involve depressing the depressible button when the screw threads are fully engaged thereby increasing the air pressure in the interior of the cup relative to the air pressure when the button is in the raised position, and thereby introducing fluid sample into the chamber. The methods can also include the step of turning the lid until the screw threads are fully engaged and the stop tabs abut one another.

In another aspect, the present invention provides methods of detecting the presence of an analyte in a liquid sample. The methods involve introducing the liquid sample into a cup of the device described herein, mounting the lid on top of the cup, allowing sample flow and observing the results of the assay the sample application zone of the assay component.

The present invention includes a variety of other useful aspects, which are detailed herein. These aspects of the invention can be achieved by using the articles of manufacture and compositions of matter described herein. To gain a full appreciation of the scope of the present invention, it will be further recognized that various aspects of the present invention can be combined to make desirable embodiments of the invention. In addition, a variety of other aspects and embodiments of the present invention are described herein.

The summary of the invention described above is not limiting and other features and advantages of the invention will be apparent from the following detailed description, as well as from the claims.

DETAILED DESCRIPTION

Sample Collection and Analysis Cup Activate by an Increase in Internal Air Pressure In the following detailed description, reference is made to the accompanying drawings that form a part hereof, and in which is shown by way of illustration specific embodiments in which the invention may be practiced. Other embodiments may be utilized and structural changes may be made without departing from the scope of the present invention.

The present invention provides an easy to use, self-activating sample collection and analysis device. After sample collection, the lid is screwed on and the device begins the assay. The device of the present invention provides advantages over more complicated urine analysis devices because very little technician contact with the sample is necessary, and virtually opportunity is provided for technician error.

Figure 1:
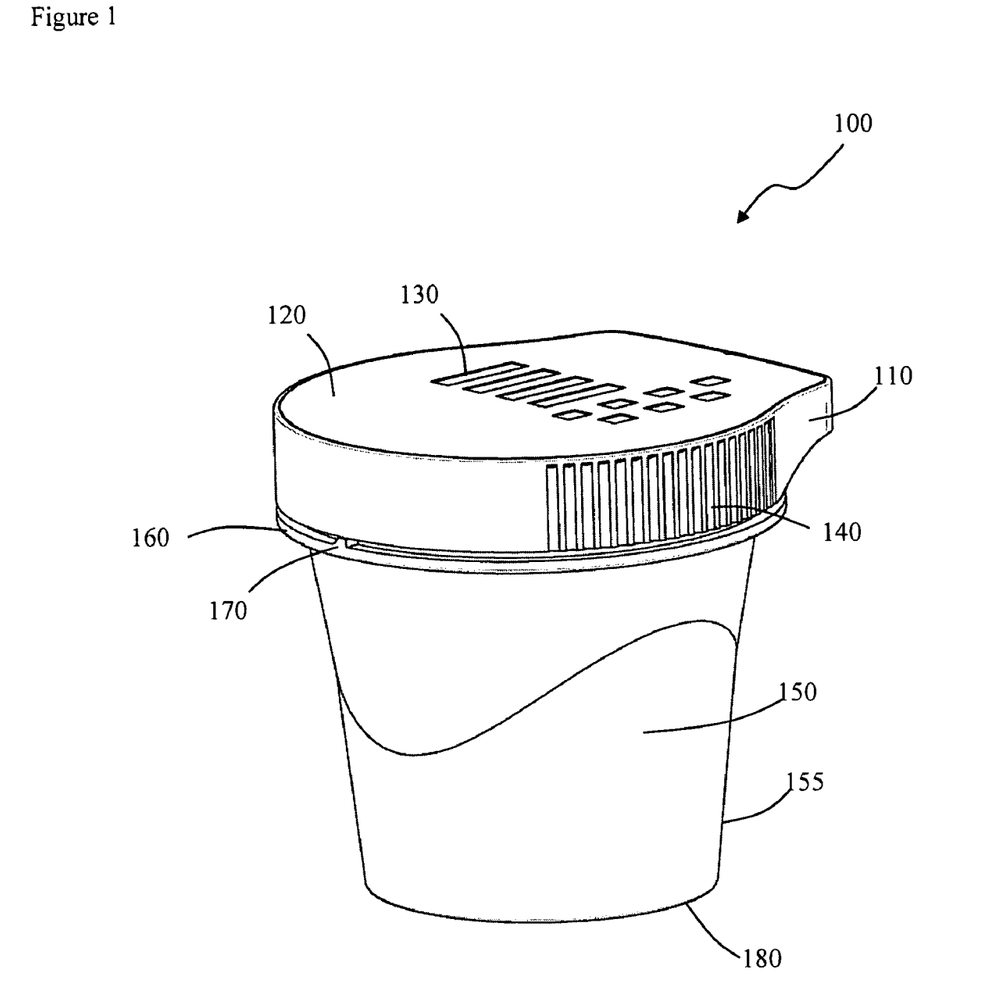
FIG. 1 provides a perspective view of the present invention, showing the cup 150 and the lid 110.
Figure 2:
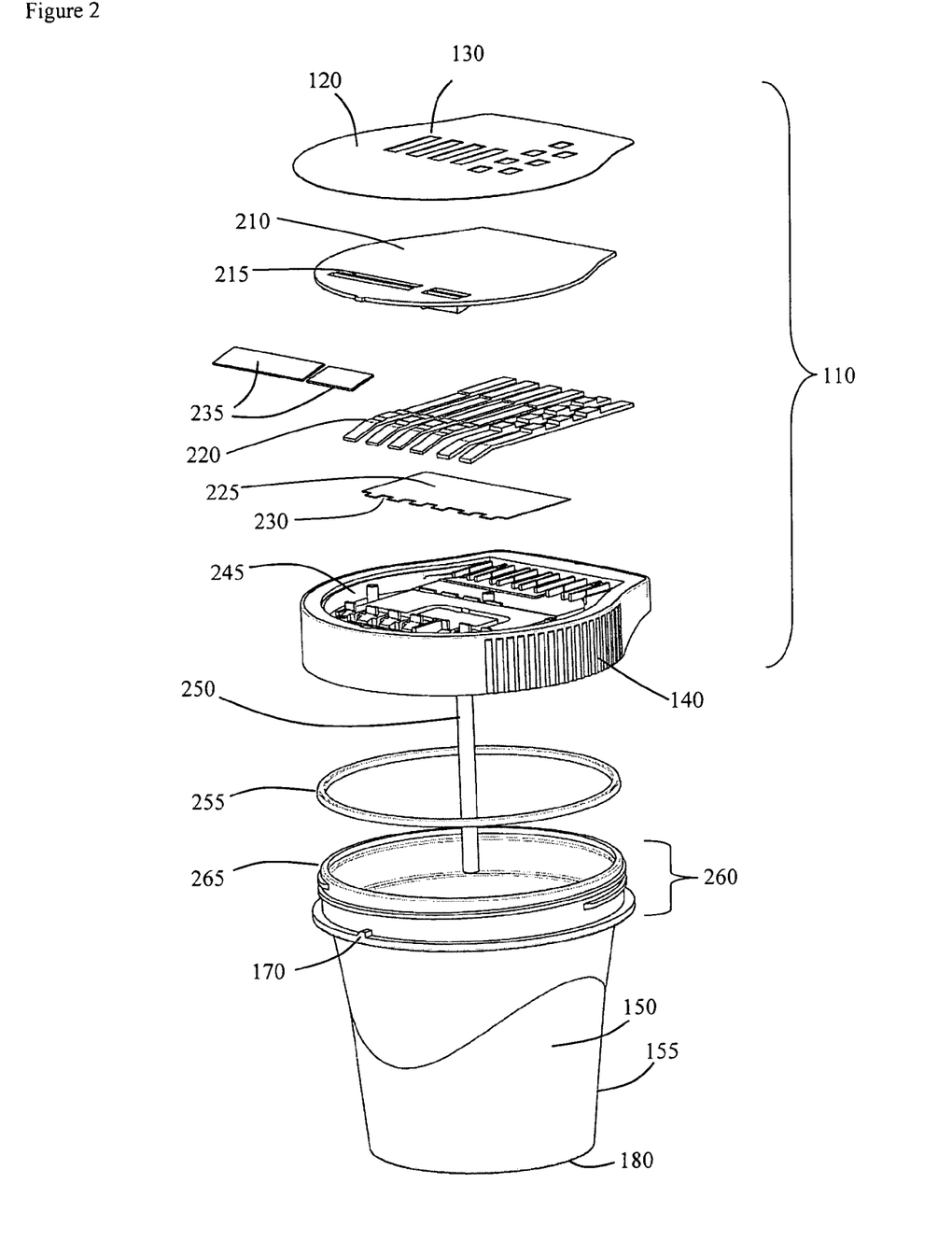
FIG. 2 is an exploded view of the device shown in FIG. 1.

FIGS. 1 and 2 show a device of the invention 100, a liquid sample collection and analysis device comprising a cup 150, a lid 110 and an O-ring 255. In this embodiment the chamber is contained in the lid. The lid may be covered with an optional adhesive sticker 120 defining one or more windows 130 for viewing test results and bearing indicia. Additionally, the lid comprises a side curtain 140. The curtain may be adapted for improved gripping with a series of bumps or ridges. The cup comprises a side wall 155 and a bottom surface 180 upon which the device may be placed. The cup is provided with a rim 260 that includes at least one stop tab 170 and a rim edge 265 (FIG. 2). Multiple stop tabs may be placed advantageously around the rim of the cup. The curtain of lid has at least one stop tab (not shown) that mates with the rim stop tab. When the curtain stop tab engages the cup stop tab, the lid has been fully screwed onto cup and an airtight seal has been created. O-ring 255 can be made of any material commonly used for O-rings, such as rubber or siliconized rubber. The O-ring is compressed between the rim of cup and the interior surface of the lid during formation of the airtight seal (see FIG. 5).

The cup and lid may be manufactured from any convenient material using manufacturing techniques know in the art. For example, the cup and lid may be made from injection molded plastic (e.g. polyethylene terephthalate, high density polyethylene, polyvinyl chloride, low density polyethylene, polypropylene or polystyrene). Alternatively, the cup may be manufactured of glass or press-molded plastic. Portions of the lid may be manufactured from plastic, rubber, paper, cardboard, foil, metal or glass and then joined to form the completed unit.

Figure 3:
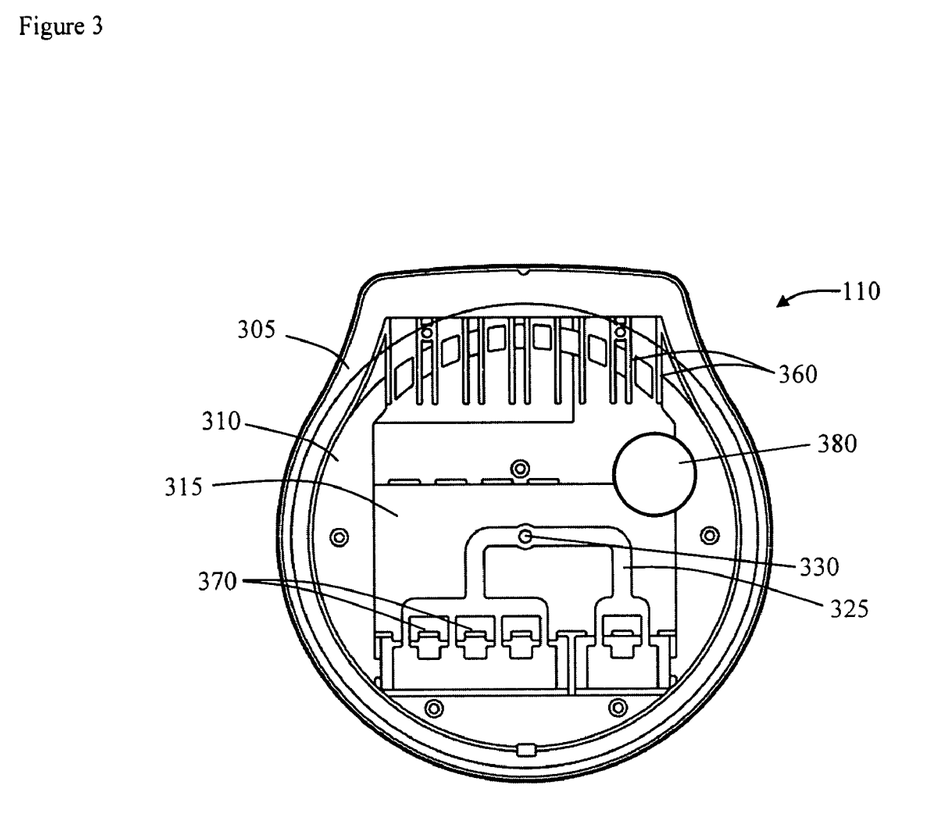
FIG. 3 provides a top view of the interior of one embodiment of the lid of the device shown in FIG. 1.

As shown in FIGS. 2 and 3, in the embodiment depicted the lid further comprises a chamber 245, defined by a floor 310, a raised platform 315, a side wall 305 and a transparent cover 210. Within the chamber are one or more test strips 220, a comb 225 and a wicking paper 235. The transparent cover provides a flat surface through which the test strips can be seen. A sticker 120, carrying indicia and having windows 130 may be placed on top of the transparent cover. Advantageously, the windows are aligned with the test strips below the transparent surface such that test results can be conveniently observed. Indicia present on the optional sticker indicate what test is conducted on each test strip and where the test results should appear on the test strip below the window.

Figure 4:
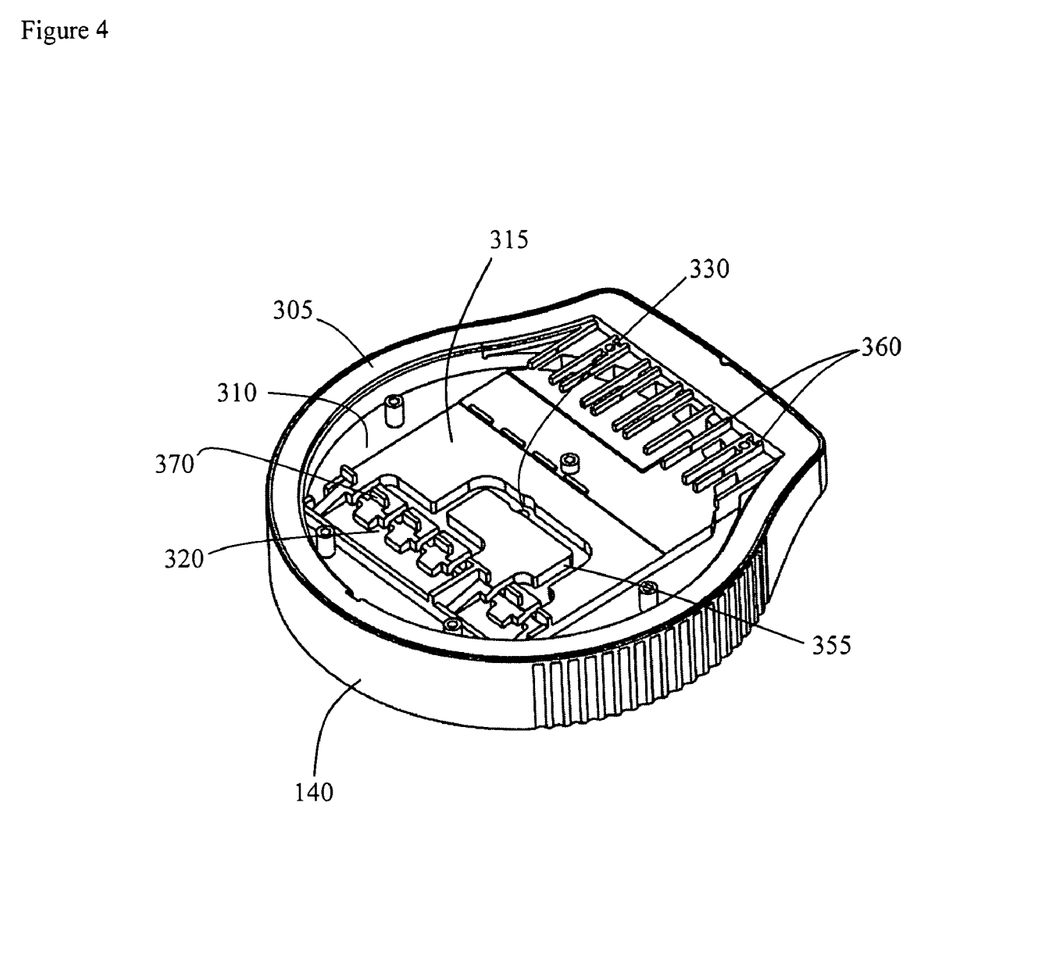
FIG. 4 provides a perspective view of one embodiment of the lid 110 of the device shown in FIG. 1.

As shown in FIGS. 3 and 4, the platform, within the chamber, further comprises a channel network 325 having a sample inlet 330. On the bottom 540 of the lid, a tube 250 is fluidly connected to the inlet by a protrusion 545 (see FIG. 5). Fluid flows from the cup, through the inlet and into the channel network. The larger channels of the channel network may be subdivided into smaller channels, which end in outlets 330. At the outlets, the sample comes into contact with the sample application zones of the test strips.

In the embodiment of FIG. 2, the comb rests on top of the platform. The test strips are supported by the comb. The comb both supports the test strips and prevents them from becoming wet by the liquid flowing through the underlying channel network. The comb has cut-outs 230 through which the sample application zone of a test strip may be downwardly bent to facilitate contact with sample flowing out of the outlets. The comb may be made of any convenient material, such as but not limited to, plastic card, a non-absorbent sticker, glass, foil, or paper, card stock or cardboard treated to be non-absorbent. "Non-absorbent" stickers, paper and card stock or card board have been treated to prevent absorption of the sample. For example, it may be plastic or wax coated or foil laminated. Alternatively, it may be coated with water-insoluble adhesive, which would adhere the comb to the platform and prevents passage of sample from the channel network directly to the back of the test strips.

The wicking paper is in fluid communication with the sample application zones of the test strips, and can also be in fluid communication with the outlets of the channel network. The wicking paper may be placed either above or below the sample application zone of the test strips. When present at the outlet, the wicking paper imbibes the fluid at the outlet and facilitates the even delivery of fluid to the test strips. The wicking paper may be any convenient absorbent material that will quickly transport sample from the channel outlets to the test strips. Suitable materials for wicking paper include, but are not limited to, 3MM paper available from Whaman Inc., Transorb® and Filtrona® brand bonded filter media supplied by Filtrona Inc., cellulose and nitrocellulose papers, treated polyester meshes and treated glass fiber or wool. It is known to those in the art that these and additional available materials can be treated using well-know techniques to change their absorbent properties. For example, hydrophobic glass fiber can be hydrophilic by treating it with one or more of protein, such as bovine serum albumin (BSA) or milk protein, buffers, such as Tris buffer or Phosphate buffered Saline, and detergent, such as sodium dodecylsulfate (SDS), Tween-20® or Triton-X 100®.

In the embodiments shown in FIGS. 2, 3, and 4, the chamber further comprises a series of guides 360. On the platform, adjacent to the outlets, are pins 370. The guides and pins work in concert to ensure correct placement of the test strips, so that the test strips align with the windows of sticker. Additionally, the guides and pins prevent movement of the test strips within the chamber. Optionally, the transparent cover may be provided with a depression 215, which downwardly press the test strips, to ensure contact with the wicking paper and/or the outlets.

In further embodiments, the lid and the cup comprise complementary annular screw threads that engage each other. The lid and the cup may be adapted for an inside screw lid or an outside screw lid. In the case of an "outside screw lid" the cup threads 510 are on the outside surface of the cup rim (See FIG. 5). The lid threads 515, which are adapted to mate with the cup threads, are on the inner surface of the lid side curtain. An inside screw lid can also be utilized with this invention. In the case of an "inside screw lid," the lid is sized and shaped so that the side curtain fits within the cup rim, in a cork-like manner. In this case, the cup screw threads are placed on the inner rim surface. The lid threads are placed on the outer surface of the lid side curtain and adapted to mate with the cup threads.

Figure 5:
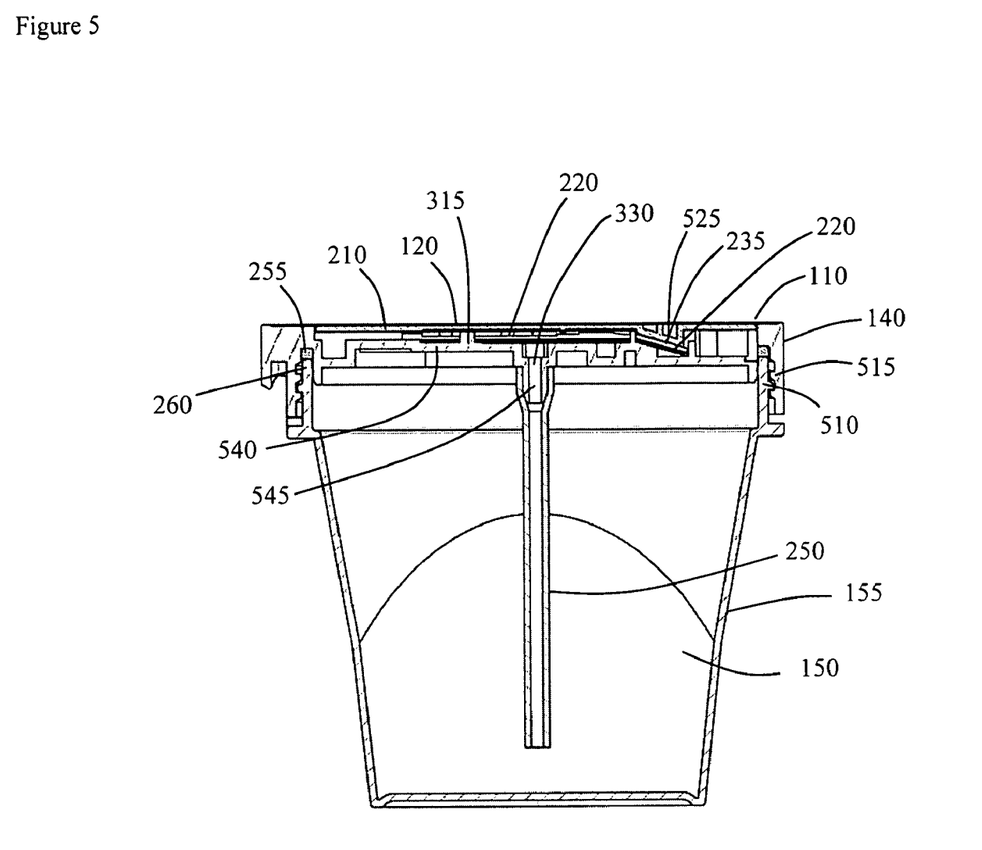
FIG. 5 is a cross-section of the device shown in FIG. 1.

FIG. 5 is a cut-away view of the present invention. The O-ring is interposed between the edge of the cup rim and the bottom surface of the lid. When the screw threads are almost fully engaged and air-tight seal is formed between the cup and the lid. The lid is screwed on until the screw threads are fully engaged and the stop tabs are mated, causing a higher internal cup air pressure relative to the air pressure of the unsealed cup. This increase in air pressure pushes a portion of sample from the interior of the cup, through the tube and into the channel network of the chamber, such that the test strips come into contact with sample and become activated.

Figure 6:
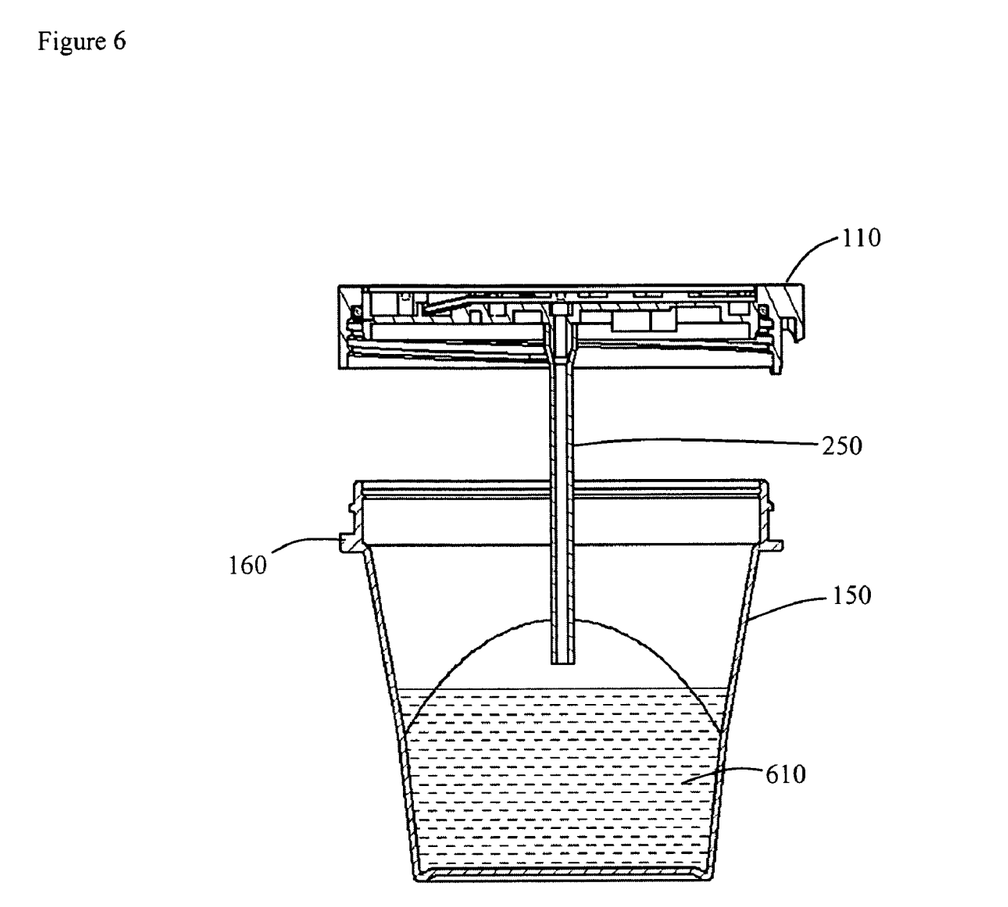
FIG. 6 illustrates a device shown in FIG. 1, and the step of placing the lid 110 on the cup 150 containing a liquid sample 610.
Figure 7:
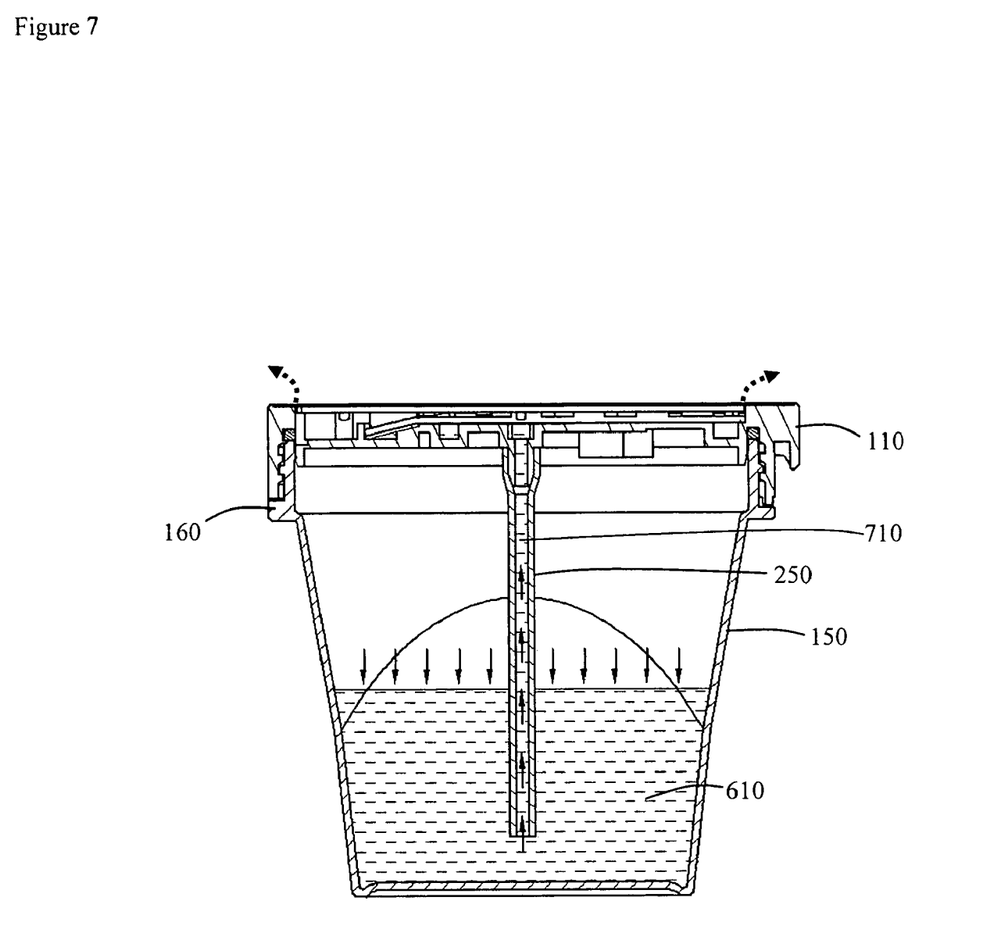
FIG. 7 illustrates increased internal air pressure, denoted by the downward facing arrows, pushing a portion of the sample 710 up the tube 250 and into the lid 110.
Figure 8:
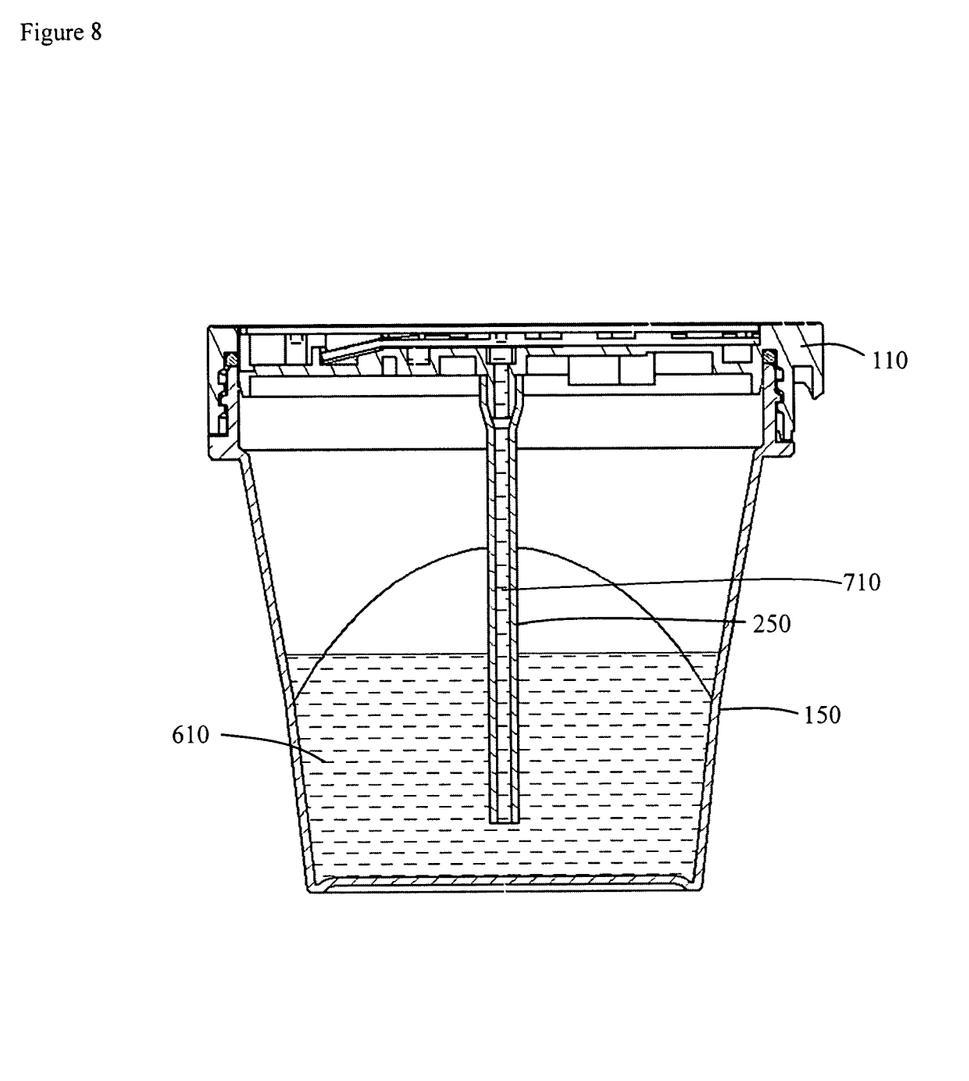
FIG. 8 illustrates the stopping of sample flow up the tube 250 after equalization of the internal air pressure.

FIGS. 6, 7 and 8 illustrate the function of the present invention in one embodiment. FIG. 6 shows an open cup containing a sample 610 and the lid, prior to being screwed onto the cup. FIG. 7 illustrates what happens when the lid is screwed onto the cup containing the sample. Air pressure has increased within the device, relative to the external air pressure. To equalize with the external air pressure, the air within the sealed cup will push on the sample (downward arrows), force a small amount of sample up tube (upward arrows) and into the channel network (see FIGS. 3 and 4). The air within the chamber that is displaced by the sample escapes around the edges of the transparent plate (dashed arrows), since the transparent plate is not airtight in this embodiment. In embodiments where the transparent plate is made air tight, a small vent hole is placed in the outer surface of the lid, for the air to escape the chamber when the sample flowed into the channel network.

Additional means of increasing the internal sealed cup air pressure relative to that of the unsealed cup may be employed. Certain embodiments of the present invention include a depressible button on the side of the cup or on the lid. The button has a depressed position and a raised position. When the screw threads are fully engaged, the button can be depressed by the operator. This causes the air pressure in the cup to increase relative to the air pressure when the button is in the raised position. The increase in internal air pressure causes sample to flow up the tube, into the channel network and to the test strips.

If the drug test result is positive, the sample is sent to another laboratory for confirmation testing. The cup may be opened by unscrewing the lid; however, re-capping the cup may reactivate the device. This can result in flooding of the chamber. To overcome this problem certain embodiments of the present invention comprise a sealable sample port (not shown). The sample port may be located on the lid or side of the cup, and can provide easy access to the liquid sample with a pipette or other instrument. The sample port is provided with either a plug seal or a screw seal, which can be replaced securely after it has been open. The seals may be made of any convenient material, such as plastic, rubber or siliconized rubber.

Test Components

A variety of test strips may be used in combination with the present device, depending upon the analytes of interest and the purpose of the tests. Test strips may be separated into two general categories, analyte test strips and adulteration test strips. Analyte test strips contain reagents for detecting an analyte of interest in the sample. Adulteration test strips contain reagents for detecting a physical property of the sample. Both types of test strips have a sample application zone and a detection zone.

Analyte test strips: A variety of analyte test strips can be incorporated into the present invention. Analyte test strips comprise an immunoassay or a chemical test and tests for an analyte of interest in the sample, such as a drug of abuse or a metabolite suggestive of health status.

A "drug of abuse" (DOA) is a drug that is taken for non-medicinal reasons (usually for mind-altering effects). The abuse of such drugs can lead to physical and mental damage and (with some substances) dependence, addiction and/or death. Examples of DOAs include cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellowjackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone).

Legal drugs that are taken for medical reasons, but on which overdose can easily occur may also be tested for using these test strips. These drugs include tricyclic antidepressants (imipramine and the like) and over the counter products containing acetaminophen (Tylenol®, McNeil-PPC, Inc., Ft. Washington, Pa.). This type of testing can aid emergency workers in determining if an unconscious of ill person has accidentally overdosed on one of these medications.

Metabolites found in urine, that may be suggestive of health status include but are not limited to creatinine, bilirubin, nitrite, protein (nonspecific), hormones (e.g. human chorionic gonadotropin, luteinizing hormone, follicle stimulating hormone, etc.), blood, leukocytes, sugar, heavy metals or toxins, bacterial components (e.g. proteins or sugars specific to a particular type of bacteria, such as *E. coli*0157:H7, *S. aureus, Salmonella, C. perfringens, Campylobacter, L. monocytogenes, V. parahaemolyticus*, or *B. cereus*) and physical characteristics of the urine sample, such as pH and specific gravity. Any other clinical urine chemistry analyte that can be adapted to a lateral flow test format may also be incorporated into the present device.

Analyte test strips are available in a variety of formats. Generally, the test strips consist of a bibulous material having a sample application zone, a reagent zone and a test result zone. The sample is applied to the sample application zone and wicks into the reagent zone by capillary action. In the reagent zone, the sample dissolves and mixes with reagents necessary for detection of the analyte (if it is present in the sample). The sample, now carrying the reagents, continues to wick to the test results zone. Additional reagents are immobilized in the test results zone. These reagents react with the analyte (if present) or one of the first reagents from the reagent zone. If the sample does contain the analyte, a signal is produced. If the analyte is not present, no signal is produced.

As a more specific example, the analyte test strips disclosed in the following references can be applied to the present invention: U.S. Pat. Nos. 5,252,496, 5,415,994, 5,559,041, 5,602,040, 5,656,503, 5,712,170, 5,877,028, 5,965,458, 5,986,895, 6,046,058, 6,136,610, 6,140,136, 6,183,972, 6,187,268, 6,187,598, 6,194,221, 6,194,224, 6,221,678, 6,228,660, 6,241,689, 6,248,598, 6,271,046, 6,297,020, 6,316,205, 6,372,514, 6,338,969, 6,368,873, 6,372,516, 6,375,896, 6,375,897, 6,391,652, 6,403,383, 6,418,606, 6,429,026, 6,464,939, 6,468,474, 6,485,982, 6,506,612, 6,514,769, 6,528,323, 6,548,019, 6,730,268, 2001/0004532, 2001/0008774, 2001/0021536, 2001/0023076, 2001/0041368, 2002/0001854, 2002/0004019, 2002/0031840, 2002/0031845, 2002/0052050, 2002/0085953, 2002/0137231, 2002/0173047, 2002/0132267, 2003/0129088, 2003/0129673, 2003/0207466, 2004/0018636, and 2004/0191760.

Adulteration test strips: Adulteration test strips test for a physical property or contamination of the sample, such as temperature, specific gravity, pH, oxidant contamination, glutaraldehyde contamination, nitrite contamination, ascorbic acid contamination or creatinine concentration. For this testing purpose it is also desirable to utilize test strips that incorporate assays that detect the addition of chemicals or other behavior intended to defeat the assay and disguise drug use. The test strips can be used in any convenient format, such as an immunoassay or a chemical test. In some embodiments, creatinine and protein assays may be included on the test strip to detect the dilution of a urine sample. B-vitamins may also be tested for, or any of glutaraldehyde, nitrites, chromate, vinegar, Visine™ (Pfizer, Inc., New York, N.Y.), sodium bicarbonate, Drano™ (S.C. Johnson, Racine, Wis.), soft drinks, oxidants such as bleach, hydrogen peroxide, pyridinium, chlorochromate, or other chemicals added to urine in attempts to defeat the assay.

Test strips that test a physical property of a sample that can be used in combination with the present invention. Such test strips comprise a bibulous material for transporting liquid sample through the test strip; a filter member in liquid communication with the bibulous material, a reagent pad in liquid communication with the filter member and optionally a transparent cover. The reagent pad contains reagents for producing a detectable signal related to a property of the sample and can be viewed through the transparent cover and the transparent plate of the device (when utilized). The filter member can be made of a material that inhibits backflow of fluid from the reagent pad to the bibulous material. By "inhibits backflow" is meant that any quantity of fluid that flows from the reagent pad to the bibulous material is not of a quantity that will change the result of the assay or transport reagents onto the bibulous material or into an neighboring reagent pad in an amount that is detectable in the assay or obscures the result of the assay. The test strips may also comprise a hydrophobic member positioned between a portion of the filter member and the bibulous material. The hydrophobic member is positioned to inhibit backflow of sample from the reagent pad into the bibulous material. The liquid sample is transported through the test strip by capillary action. "Capillary action" refers to the well-known physical effect caused by the interactions of a liquid with the walls or interior of a material, which results in a movement of the liquid through the material. By a "bibulous material" is meant a material that readily absorbs or imbibes fluids and in which capillary action serves to transport the fluid to other portions of the material. A "filter member" promotes even distribution of liquid sample as sample flows to the reagent pad. This in turn promotes an even development of detectable signal in the reagent pad. The filter member also inhibits backflow of sample from the reagent pad to the bibulous material, and therefore also inhibits movement of reagent chemicals from one reagent pad to another. By a "hydrophobic member" is meant a member that does not allow the passage of a quantity of fluid that would alter the result of the assay. The hydrophobic member will usually be a hydrophobic barrier to fluid movement.

Other types of capillary flow adulteration test strips may be incorporated into the present device. For example, the adulteration test strips disclosed in the following references can be applied to the present invention, U.S. Pat. Nos. 2002/0001845, 2002/0098512, 2002/0155028, 2003/0045003, U.S. Pat. Nos. 5,922,283, 6,248,598, 6,514,768, 6,537,823, and 6,548,019.

Types of Samples

Samples that can be tested with the device of the present invention include liquids of biological origin (e.g., body fluids and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other body of water, effluent samples, soil samples, ground water, ocean water, and runoff water. Sewage and related wastes can also be included as environmental samples.

Methods of Use

Another aspect of the present invention is a method of detecting the presence of an analyte in a fluid sample, using the device described above. FIGS. 6 through 8 illustrate some of the steps of this method. This method includes the following steps. First, a liquid sample is introduced into the cup (FIG. 9). The lid is applied to the cup. In embodiments where screw threads are used, the lid is tightened until the screw threads are fully engaged. A pressure gradient is thereby created and fluid sample is forced into the tube and on to the chamber, where a test component is present, such as a test strip (FIGS. 7 and 8). If the device is provided with a depressible button as described above, the button would be depressed after sealing the lid on the cup.

As described above, in one embodiment the cup and the lid have engageable screw threads. When screw threads are fully engaged, a seal is created and the internal air pressure of the device will be higher relative to the air pressure of the device prior to fully engaging threads. The cup and the lid may also have mate-able stop tabs. In these embodiments, the lid is screwed onto the cup until the stop tabs abut one another, and a seal is created, resulting in an increased internal air pressure. The increase in internal air pressure forces sample 710 up the tube, from the cup into the chamber.

EXAMPLE 1

This example describes a use of a device of the invention to detect morphine, opiates, and THC in urine. This embodiment utilized a cup having stop tabs and complementary screw threads on the lid and rim of the cup. Three lots of 10 devices each were tested. Normal urine spiked with a THC standard, an opiate (OPI) standard, and a morphine (MOP) standard at concentrations of 0×, 0.5×, 1.5× and 3× times the detection limit was used. For example, the detection limit of the THC test is 50 ng/ml, so urine containing 0 ng/ml, 25 ng/ml, 75 ng/ml and 150 ng/ml of THC was tested. The OPI test detection limit is 2000 ng/ml and urine containing 0 ng/ml, 1000 ng/ml, 3000 ng/ml and 6000 ng/ml OPI was tested. Similarly, the MOP test detection limit is 300 ng/ml, so urine containing 0 ng/ml, 150 ng/ml, 450 ng/ml and 900 ng/ml MOP were tested.

Four ml to 6 ml of urine was poured into the cup and the lid screwed onto the cup until the tabs mated. The urine was observed to flow up the tube and the test strips became wet as fluid flowed through the wick and the test strips. The test results are shown in the table below.

| Drug | Negative | 0.5X | 1.5X | 3X |
|---|---|---|---|---|
| THC (50 ng/ml) | negative | weak negative | positive | very strong positive |
| OPI (2000 ng/ml) | negative | weak negative | positive | very strong positive |

-continued

| Drug | Negative | 0.5X | 1.5X | 3X |
|---|---|---|---|---|
| MOP (300 ng/ml) | negative | weak negative | positive | very strong positive |

Urine containing no drug always gave a negative result. Urine containing an amount of drug below the detection limit of the test produced weak negative test results. Urine with drug at concentrations higher than the lower detection limit produced positive test results.

EXAMPLE 2

Pre-Employment Drug Screening

The devices of the invention can be utilized in a variety of contexts, for example, for pre-employment drug screening. The person to be tested provides a sample of urine in a device of the invention. In embodiments for pre-employment drug screening the device contains test strips for several common drugs of abuse, in this embodiment morphine, amphetamines, barbiturates, LSD, phencyclidine, and opiates. These test strips utilize an immunoassay format where if analyte is present in the sample it is bound by specific binding molecules on the test strip and by labeling molecules, thereby forming a line on the test strip (although other embodiments may use a chemical or color development test. The device also contains physical assay so for temperature, glutaraldehyde, and creatinine to detect adulteration. After receiving the sample, the testing technician mates the lid of the cup with the cup rim, both of which contains screw threads. The lid is tightened onto the cup until stop tabs located on the lid and rim are met and abut one another. At this point the assay has begun, as pressure is increased inside the device and urine is forced upward through the passage and into the chamber, which contains the test strips. Within about 30 seconds urine has traveled through the test strips and the assay is complete. In embodiments using immunoassays, the technician compares the development of control and analyte lines on the test strip of the device with a master chart. In embodiments using color development the technician compares the color development on the test strips with colors provided on a master chart, thereby obtaining the result of the assay.

In other embodiments the devices are useful for medical testing in a medical office or laboratory. In these embodiments the device may include test strips for sugar, protein, creatinine, blood, and pH. Additionally, the devices are useful for testing for the presence of any analyte or chemical for which a test component exists and can be incorporated into the device. With reference to the present disclosure, the person of ordinary skill will realize many useful testing formats.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A liquid sample collection and analysis device, comprising:
   a cup having an interior for containing a liquid sample;
   a lid that forms an airtight seal when secured to the cup;
   a chamber for holding liquid sample and containing a test component containing reagents for detecting an analyte of interest in the sample, the test component having a sample application zone and a detection zone;
   a tube providing a passage between the interior of the cup and the chamber, for transport of a portion of the liquid sample from the interior of the cup into the chamber due to air pressure exerted on the surface of the liquid sample by application of the lid to the cup.

2. The device of claim 1 wherein the chamber is contained within the lid and comprises a channel having an inlet for receiving liquid sample from the tube.

3. The device of claim 2 wherein the channel further comprises an outlet for delivering liquid sample from the inlet to the test component.

4. The device of claim 3 wherein the chamber further comprises wicking paper in fluid communication with the outlet and the sample application zone of the test component.

5. The device of claim 1 wherein the lid and the cup comprise screw threads and, when the screw threads are fully engaged, an airtight seal is formed between the cup and lid.

6. The device of claim 5 wherein the cup and lid further comprise stop tabs that abut one another when the screw threads are fully engaged.

7. The device of claim 5 further comprising a depressible button having a depressed position and a raised position such that, when the screw threads are fully engaged, air pressure in the cup is higher when the button is in the depressed position relative to the air pressure when the button is in the raised position.

8. The device of claim 1 wherein the test component is a test strip comprising specific binding molecules immobilized on the test strip.

9. The device of claim 1 further comprising a sealable opening in the lid for extracting liquid sample when the lid is mated to the cup.

10. The device of claim 1 wherein the test components are test strips and wherein the lid comprises a plurality of test strips for determining the presence or absence of a plurality of analytes of interest in the sample.

11. The device of claim 10 wherein said test strips comprise an immunoassay.

12. The device of claim 10 wherein said test strips comprise a chemical test.

13. The device of claim 10 further comprising a test strip for determining a physical property of the liquid sample.

14. The device of claim 13 wherein the physical property is selected from the group consisting of one or more of: temperature, specific gravity, pH, oxidant contamination, glutaraldehyde contamination, nitrite contamination, ascorbic acid contamination and creatinine concentration.

15. The device of claim 1 wherein the lid is principally flat on one side.

16. A liquid sample collection and analysis device, comprising:
   a cup comprising an interior for containing a liquid sample and a rim having first screw threads and a first stop tab;
   a lid comprising a chamber, a test strip having a sample application zone and a detection zone, a transparent window and a side curtain having second screw threads and a second stop tab; and
   a tube in fluid communication with the interior of the cup and the chamber, for transporting a portion of the liquid sample from the cup interior into the chamber in response to an increase in internal air pressure in the device caused by application of the lid to the cup.

17. The device of claim 16, the chamber further comprising:
   a channel network having an outlet and an inlet in fluid communication with the tube; and
   a wicking paper in fluid communication with the outlet and the sample application zone of the test strip.

18. The device of claim 16, wherein when the first and second screw threads are fully engaged an airtight seal is formed between the cup and the lid.

19. The device of claim 18, the cup further comprising a depressible button, the button being adapted to be manually depressed by the operator, the closed cup with a depressed button having a higher internal air pressure relative to a closed cup with an un-depressed button.

20. The device of claim 16, wherein when the first and second stop tabs are mated an airtight seal is formed between the cup and the lid.

21. The device of claim 20, the cup further comprising a depressible button, the button being adapted to be manually depressed by the operator, the closed cup with a depressed button having a higher internal air pressure relative to a closed cup with an un-depressed button.

22. The device of claim 16 further comprising a sealable opening in the lid for extracting liquid sample when the lid is mated to the cup.

23. The device of claim 16 wherein the test strip comprises specific binding molecules immobilized on the test strip.

24. The device of claim 16, the test strip further comprising a chemical test.

25. The device of claim 16, the test strip further comprising an immunoassay.

26. The device of claim 16 wherein the test results can be visually determined.

27. The device of claim 16 wherein the test strip determines a physical property of the liquid sample.

28. The device of claim 27 wherein the physical property is selected from the group consisting of one or more of: temperature, specific gravity, pH, oxidant contamination, glutaraldehyde contamination, nitrite contamination, ascorbic acid contamination and creatinine concentration.

* * * * *